United States Patent [19]

Volkmann et al.

[11] Patent Number: 5,132,300
[45] Date of Patent: Jul. 21, 1992

[54] BETA-LACTAM ELASTASE INHIBITORS

[75] Inventors: Robert A. Volkmann, Mystic; V. John Jasys, New London, both of Conn.; Michael S. Kellogg, Barington Hills, Ill.

[73] Assignee: Pfizer Inc., New York, N.Y.

[21] Appl. No.: 359,548

[22] Filed: Jun. 1, 1989

[51] Int. Cl.⁵ ............... C07D 513/02; C07D 499/00; A61K 31/385
[52] U.S. Cl. .................. 514/192; 514/210; 540/303; 540/304; 540/310
[58] Field of Search ............ 540/310, 304, 303, 310, 540/312; 514/210, 192

[56] References Cited

U.S. PATENT DOCUMENTS 4,797,396 1/1989 Finke et al. .................. 540/310
4,847,247 7/1989 Thompson et al. ............ 540/310

Primary Examiner—Nicholas S. Rizzo
Attorney, Agent, or Firm—Peter C. Richardson; Lawrence C. Akers; Howard R. Jaeger

[57] ABSTRACT

Novel beta lactam compounds having potent elastrase inhibition activity are disclosed. These compounds are characterized by the general structural formulae I, II, and III:

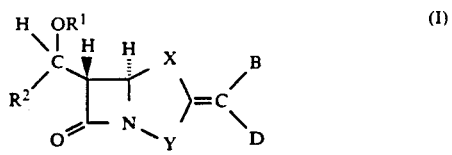

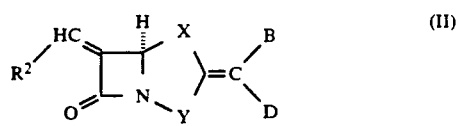

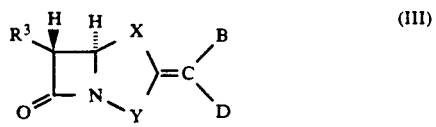

These compounds are further characterized such that X and Y are each —S— or —$CH_2$—, with at least one of X and Y being —S—, or alternatively, X is —SO— or —$SO_2$— and Y is —$CH_2$—; $R^1$ is hydrogen, tri(lower alkyl)silyl, —COOR'' or —CONHR''', wherein R'' and R''' are each lower alkyl or phenyl(lower alkyl), and may be the same or different; $R^3$ is hydrogen, lower alkyl or (lower alkyl)oxy; one of B and D is (lower alkyl)oxycarbonyl, (lower alkenyl)oxycarbonyl, allyloxycarbonyl or phenyl(lower alkyl)oxycarbonyl; and the other of B and D is hydrogen or lower alkyl.

The compounds are useful as anti-inflammatory agents, particularly in the treatment of adult respiratory distress syndrome and rheumatoid arthritis.

23 Claims, No Drawings

BETA-LACTAM ELASTASE INHIBITORS

FIELD OF THE INVENTION

This invention relates to novel beta-lactam compounds which demonstrate potent elastase inhibition activity.

BACKGROUND OF THE INVENTION

Human polymorphonuclear leukocyte elastase is the enzyme primarily responsible for the destruction of lung tissue observed in pulmonary emphysema. In addition to emphysema, human leukocyte elastase is a suspected contributor to the pathogensis of disease states such as adult respiratory distress syndrome and rheumatoid arthritis.

Proteases are an important group of enzymes in the class of peptide-bond cleaving enzymes. These enzymes are essential for a variety of normal biological activities, including digestion, formation and dissolution of blood clots, the formation of active forms of hormones, the immune reaction to foreign cells and organisms, and in the body's response to various pathological conditions, such as pulmonary emphysema and rheumatoid arthritis.

Elastase, one of the proteases, is an enzyme able to hydrolyze elastin, a component of connective tissue. This property is not shared by the bulk of the proteases present in the body. Elastase acts on a protein's nonterminal bonds which are adjacent to an aliphatic amino acid. Of particular interest is neutrophil elastase, which exhibits a broad spectrum of activity against natural connective tissue substrates. In particular, the elastase of the granulocyte is important because granulocytes are participants in acute inflammation and in acute exacerbation of chronic forms of inflammation which characterize many major inflammatory diseases.

Proteases from granulocytes and macrophages are reported to be responsible for the chronic tissue destruction mechanisms associated with such inflammatory diseases as pulmonary emphysema, rheumatoid arthritis, bronchial inflammation, osteo arthritis, spondylitis, lupus, psoriasis, and acute respiratory distress syndrome. Proteases can be inactivated by inhibitors which bind tightly to enzymes to block their active sites. Naturally occuring protease inhibitors are part of the body's defense mechanism which are vital to the maintence of a state of well being. Without such a natural defense mechanism, the proteases would destroy any protein with which they came in contact. Naturally occuring enzyme inhibitors have been shown to have appropriate configurations which allow them to bind tightly to the enzymes. Thus, specific and selective inhibitors of the proteases are excellent candidates for potent anti-inflammatory agents useful in the treatment of the above conditions.

Proteases from granulocytes, leukocytes and macrophages are participants in a three-stage chain of events which occur during the progression of an inflammatory condition. During the first stage a rapid production of prostaglandins (PG) and related compounds synthesized from arachidonic acid occurs. The evidence suggests that protease inhibitors prevent PG production. During the second stage of progression of an inflammatory condition, a change in vascular permeability occurs, which causes a leakage of fluid into the inflammed site, which results in edema. The extent of edema is generally used as a means for measuring the progression of the inflammation. The process can be inhibited by various synthetic proteases inhibitors. The third stage of progression of an inflammatory condition is characterized by an appearance and/or presence of lymphoid cells, especially macrophages and polymorphonuclear leukocytes (PMN). It has been shown that a variety of proteases and released from the macrophages and PMN, thus indicating that the proteases play an important role in inflammation.

Rheumatoid arthritis is a degenerative inflammatory condition characterized by a progressive destruction of articular cartilage both on the free surface bordering the joint space and at the erosion front built up by synovial tissue toward the cartilage. This destructive process has been attributed to the protein-cutting enzyme elastase which is a neutral protease present in human granulocytes. This conclusion si supported by observations that there is an accumulation of granulocytes at the cartilage/pannus junction in rheumatoid arthritis and by recent investigation of the mechanical behavior of cartilage in response to attack by purified elastase which has shown the direct participation of granulocyte enzymes, especially elastase, in rheumatoid cartilage destruction.

The elastase inhibitory properties of several beta-lactam compounds is known in the art. U.S. Pat. No. 4,465,687 discloses N-acyl-derivatives of thienamycin esters and their use as anti-inflamatory agents.

U.S. Pat. No. 4,493,839 discloses derivatives of 1-carbapenem-3-carboxylic esters and their use as anti-inflammatory agents.

U.S. Pat. No. 4,495,197 discloses derivatives of N-carboxyl-thienamycin esters and analogs thereof and their use as anti-inflammatory agents.

U.S. Pat. No. 4,547,371 discloses substituted cephalosporin sulfones and their use as anti-inflammatory and anti-degenerative agents.

European Patent 124,081 discloses 3-substituted-3-cephem-4-carboxylate 1,1-dioxides and their use as anti-inflammatory and anti-degenerative agents.

SUMMARY OF THE INVENTION

According to the invention, beta-lactam compounds of the general formulae I, II and III are provided:

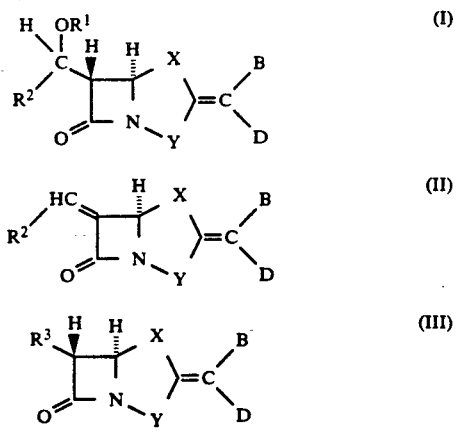

wherein X and Y are each —S— or —CH$_2$—, with at least one of X and Y being —S—; or alternatively, X is —SO— or —SO$_2$— and Y is —CH$_2$—; R$^1$ is selected from the group consisting of hydrogen, tri(lower alkyl)-silyl, —COOR″ and -CONHR‴, wherein R″ and R‴ are each selected from the group consisting of lower alkyl and phenyl(lower alkyl), and may be the same or different: R³ is selected from the group consisting of hydrogen, lower alkyl and (lower alkyl)oxy: one of B and D is selected from the group consisting of (lower alkyl)oxycarbonyl, (lower alkenyl)oxycarbonyl, allyloxycarbonyl and phenyl(lower alkyl)oxycarbonyl; and the other of B and D is one selected from the group consisting of hydrogen and lower alkyl.

The invention also provides pharmaceutical compositions comprising a compound of the general formula I, II, or III, together with a pharmaceutically acceptable diluent or carrier.

The invention further provides a compound of the general formula I, II, or III for use in treating pulmonary emphysema and rheumatoid arthritis in humans.

The invention still further provides a method of treatment of adult respiratory distress syndrome and related inflammatory conditions, especially pulmonary emphysema, and for treatment of rheumatoid arthritis comprising administering an effective amount of a compound of the general formula I, II, or III to a human being.

DETAILED DESCRIPTION OF THE INVENTION

As used herein, terms such as alkyl, alkenyl, etc., include both straight chain and branched groups, except where expressly indicated to the contrary. The term lower prefixed to any of the above terms is used to denote groups of the described type containing from 1 to 6 carbon atoms, i.e. $C_1$-$C_6$.

In the compounds of the general formulae I, II and III, $R^1$ is preferably hydrogen, (t-butyl)dimethylsilyl, t-butoxycarbonyl, benzyloxycarbonyl or benzylaminocarbonyl: $R^2$ is preferably methyl: B is preferably t-butoxycarbonyl: and D is preferably hydrogen.

Compounds demonstrating the greatest activity, and hence which are most preferred, are those wherein both X and Y are —S—, and wherein the other substituent groups are selected from among the preferred choices indicated above.

The compounds of general formulae I, II and III are prepared by several synthesis routes according to the invention.

For example, a compound (ID) of the general formulae I wherein both X and Y are —S—: $R^1$ is hydrogen; $R^2$ is methyl B is t-butyoxycarbonyl and D is hydrogen may be prepared as follows:

$$\text{LiN(Si(CH}_3\text{)}_3\text{)}_2 + \text{CH}_3\overset{\overset{\text{O}}{\|}}{\text{C}}\text{OC(CH}_3\text{)}_3 + \text{CS}_2 + \quad \text{(IA)}$$

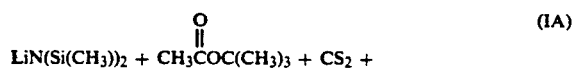

(IA) + NaH + THF + \hspace{4cm} (IB)

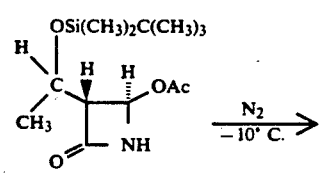

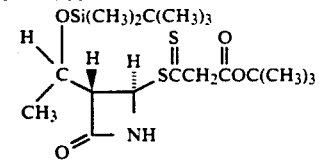

(IB) + NCS + ((CH₃)₂CH)₂NCH₂CH₃ $\xrightarrow[-20° \text{C.}]{\text{CH}_2\text{Cl}_2}$ (IC)

(IC) $\xrightarrow[\text{TBAF}]{\begin{array}{c}\text{N}_2\\\text{THF}\\\text{HOAc}\end{array}}$ (ID)

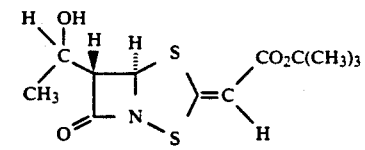

The intermediate of formula IA is prepared by reacting a strong base such as lithium bis(trimethylsilyl)amide, together with tertiary butyl acetate, carbon disulfide and tributyl tin chloride in a non-protic solvent such as tetrahydrofuran (THF) and under an inert atmosphere. This reaction is typically carried out at a low temperature, for example, about −75° C. to −80° C., for the next step.

The resulting intermediate of formula IA is reacted with 3R, 4R-4-acetoxy-3-[1R-(dimethyl-t-butyl-siloxy)ethyl]-2-azetidinone, a strong base such as sodium hydride and a non-protic solvent such as THF under an inert atmosphere to produce the intermediate of formula IB. This reaction is typically carried out at a temperature of around −10° C.

The intermediate of formula IB is allowed to react with n-chlorosuccinimide (NCS) and a base such as diisopropylethylamine in a non-protic solvent such as dichloromethane and under an inert atmosphere to produce the intermediate of formula IC. This reaction is typically carried out at a low temperature of around 0° C. to −20° C. A certain amount of the less preferred isomer in which B is hydrogen and D is t-butoxycarbonyl will also be formed. The selectivity for the preferred isomer IC is increased at lower reaction temperatures.

Finally, the intermediate of formula IC is converted in the presence of a non-protic solvent such as THF, acetic acid and tetrabutylammonium fluoride (TBAF) and under an inert atmosphere to the compound of formula ID.

Compounds identical to ID except for B being a different ester group may be prepared by preparing and utilizing the appropriate intermediate IA.

Other products of the general formula I and products of the general formula II are obtainable by the further reaction of the final product of the foregoing reaction synthesis with an appropriate electrophile in the presence of a strong base, such as dimethylaminopyridine, in accordance with the following:

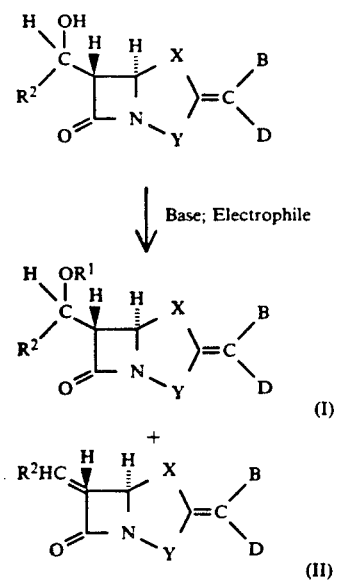

The resulting compounds of formulae I and II may be separated by silica gel chromatography.

The compound of formula I produced depends on the nature of the electrophile, as shown in the accompanying Table 1.

TABLE 1

| Electrophile | R¹ |
|---|---|
| $C(CH_3)_3C(O)-Cl$ | $-C(O)-C(CH_3)_3$ |
| $Cl-C(O)-O-CH_2-C_6H_5$ | $-C(O)OCH_2-C_6H_5$ |
| $C_6H_5-CH_2N=C=O$ | $-C(O)NHCH_2-C_6H_5$ |

Compounds of the general formulae I and II wherein one of B and D is lower alkyl rather than hydrogen may be prepared by the synthesis routes described above with the use of an appropriate t-butyl ester other than t-butyl acetate.

A compound (IF) of general formula I, wherein X is —CH₂— and Y is —S—; R¹ is hydrogen R² is methyl B is t-butoxycarbonyl and D is hydrogen may be prepared as follows:

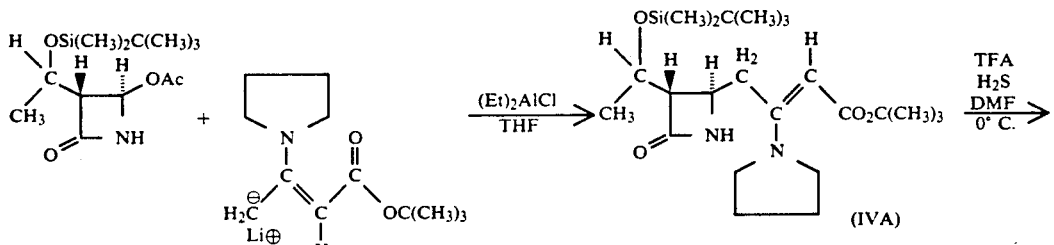

J. Antibiotics, 36, 1034 (1983)

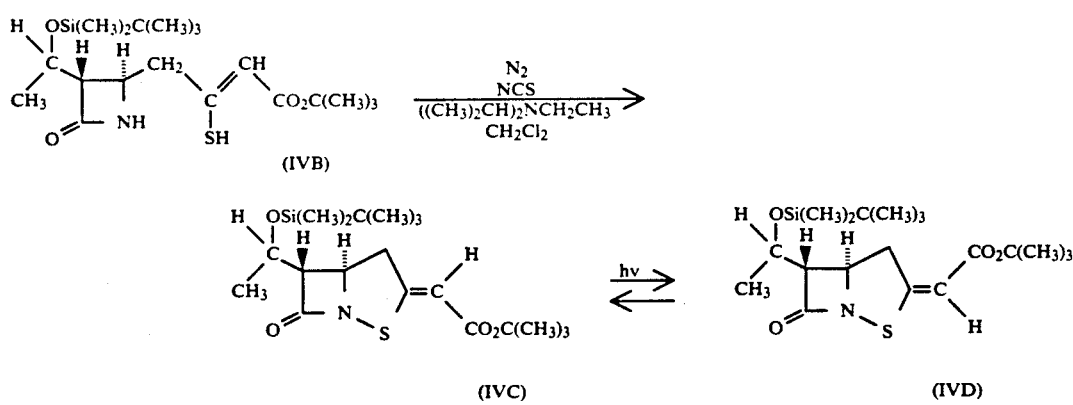

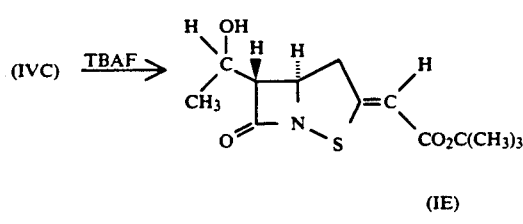

(IVD) 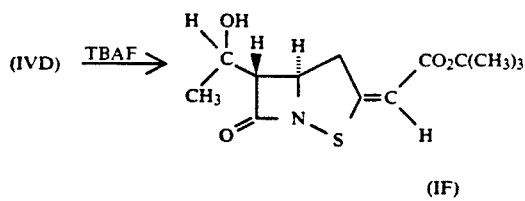 (IF)

The conversion of intermediate IVA to intermediate IVB is carried out in the presence of a strong acid such a trifluoroacetic acid (TFA) and bubbling H₂S at about

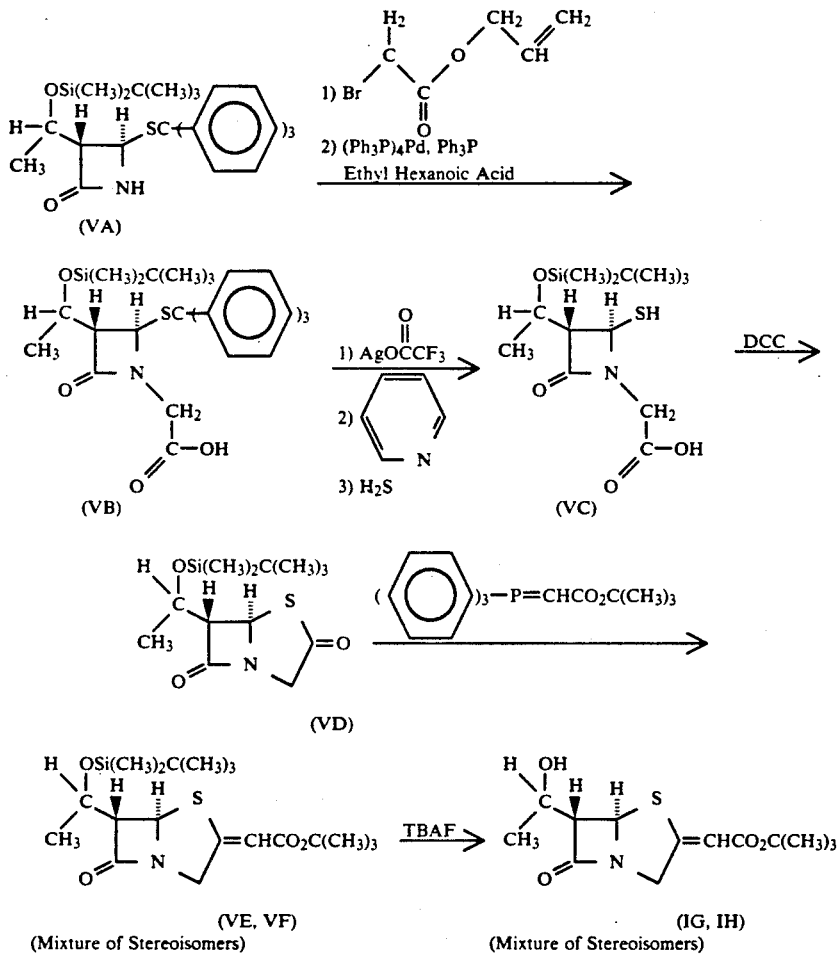
(Mixture of Stereoisomers)     (Mixture of Stereoisomers)

0° C., in a polar solvent such a dimethylformamide (DMF). Following silica gel chromatography, the compound IVB is allowed to react with n-chlorosuccinimide (NCS) and a base such as diisopropylethylamine in a non-protic solvent such as dichloromethane and under an inert atmosphere to produce a mixture of a major proportion of compound IVC and a minor proportion of compound IVD.

The two compounds of formulae IVC and IVD are stereoisomers which are reversibly convertible by photolysis.

The compounds of formulae IVC and IVD may be desilylated in the same manner as described earlier herein and, if desired, subsequently subjected to electrophillic substitution, also as described above.

Compounds (IG, IH) of general formula I, wherein X is —S— and Y is —CH₂—; R¹ is hydrogen; R² is methyl and, in the case of (IG), B is t-butoxycarbonyl and D is hydrogen and, in the case of (IH), B and D are vice versa, may be prepared according to the following reaction scheme:

The first step of this synthesis is the alkylation of VA by a haloallylacetate, followed by palladium-catalyzed deallylation to yield VB. Compound VB is converted to compound VC under standard detritylation conditions (e.g. using silver trifluoroacetate and pyridine, followed by H₂S treatment). Conversion of VC to thiolactone VD is carried out using dicyclohexylcarbodiimide (DCC) in an aprotic solvent such as dichloromethane. Standard Wittig olefination is used to generate the stereoisomeric mixture of compounds VE and VF. This stereoisomeric mixture may then be disilylated under standard conditions and the resulting mixture of compounds IG and IH separated by silica gel chromatography. It is, however, preferred to first separate VG and VF by silica gel chromatography and then desilylate each stereoisomer separately.

It is understood that compounds of general formula III may be prepared by conventional synthetic routes from the appropriate 3-substituted-4-acetoxy-azetidin-2-ones.

Still other compounds of interest are obtainable by treating those compounds of formulae I, II, and III of the invention in which X is —S— and Y is —CH$_2$— to oxygenate the thia group X.

Thus, for example,

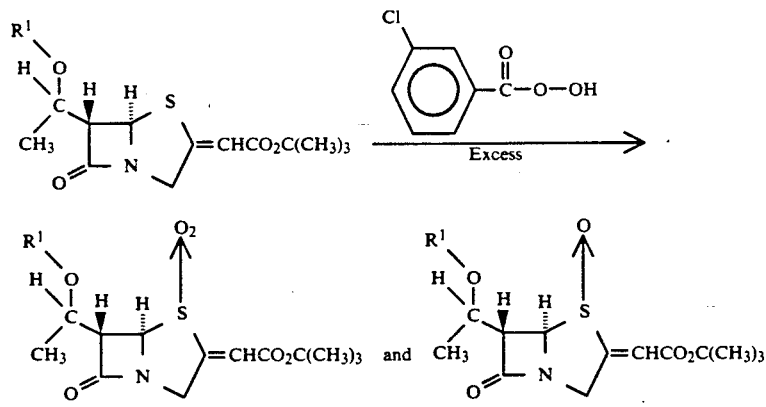

Representative compounds of the general formulae I, II and III, prepared in accordance with the invention, are listed in Table 2:

TABLE 2

| Formula | R$^1$ | R$^2$ | R$^3$ | X | Y | B | D |
|---|---|---|---|---|---|---|---|
| I | H | —CH$_3$ | — | —S— | —S— | —CO$_2$C(CH$_3$)$_3$ | H |
| I | H | —CH$_3$ | — | —S— | —S— | —CO$_2$C(CH$_3$)$_3$ | —CH$_3$ |
| I | H | —CH$_3$ | — | —S— | —S— | H | —CO$_2$C(CH$_3$)$_3$ |
| I | H | —CH$_3$ | — | —S— | —S— | H | —CO$_2$CH$_2$—C$_6$H$_5$ |
| I | H | —CH$_3$ | — | —S— | —S— | —CO$_2$(CH$_2$)CH=CH$_2$ | H |
| I | H | —CH$_3$ | — | —S— | —S— | —CO$_2$CH$_2$—C$_6$H$_5$ | H |
| I | H | —CH$_3$ | — | —S— | —S— | —CO$_2$(CH$_2$)$_2$CH$_2$—C$_6$H$_5$ | H |
| I | C$_6$H$_5$—CH$_2$NHCO— | —CH$_3$ | — | —S— | —S— | —CO$_2$C(CH$_3$)$_3$ | H |

TABLE 2-continued

| | | | | | | |
|---|---|---|---|---|---|---|
| I | ⌬—CH₂OCO— | —CH₃ | — | —S— | —S— | —CO₂C(CH₃)₃ | H |
| I | ⌬—(CH₂)₃OCO— | —CH₃ | — | —S— | —S— | —CO₂C(CH₃)₃ | H |
| I | ⌬—(CH₂)₃NHCO— | —CH₃ | — | —S— | —S— | —CO₂C(CH₃)₃ | H |
| I | (CH₃)₃COCO— | —CH₃ | — | —S— | —S— | —CO₂C(CH₃)₃ | H |
| I | (CH₃)₃C(CH₃)₂Si— | —CH₃ | — | —S— | —S— | —CO₂C(CH₃)₃ | H |
| I | H | —CH₃ | — | —CH₂— | —S— | —CO₂C(CH₃)₃ | H |
| I | H | —CH₃ | — | —CH₂— | —S— | H | —CO₂C(CH₃)₃ |
| I | ⌬—(CH₂)₃OCO— | —CH₃ | — | CH₂— | —S— | —CO₂C(CH₃)₃ | H |
| I | ⌬—(CH₂)OCO— | —CH₃ | — | —CH₂— | —S— | —CO₂C(CH₃)₃ | H |
| I | (CH₃)₃C(CH₃)₂Si— | —CH₃ | — | —CH₂— | —S— | —CO₂C(CH₃)₃ | H |
| I | (CH₃)₃C(CH₃)₂Si— | —CH₃ | — | —CH₂— | —S— | H | —CO₂C(CH₃)₃ |
| I | H | —CH₃ | — | —S— | —CH₂— | —CO₂C(CH₃)₃ | H |
| I | H | —CH₃ | — | —S— | —CH₂— | H | —CO₂C(CH₃)₃ |
| I | ⌬—CH₂NHCO— | —CH₃ | — | —S— | —CH₂— | —CO₂C(CH₃)₃ | H |
| I | (CH₃)₃C(CH₃)₂Si— | —CH₃ | — | —S— | —CH₂— | H | —CO₂C(CH₃)₃ |
| I | (CH₃)₃C(CH₃)₂Si— | —CH₃ | — | —S— | —CH₂— | —CO₂C(CH₃)₃ | H |
| I | ⌬—CH₂NHCO— | —CH₃ | — | —SO— | —CH₂— | —CO₂C(CH₃)₃ | H |
| I | ⌬—CH₂NHCO— | —CH₃ | — | —SO₂— | —CH₂— | —CO₂C(CH₃)₃ | H |
| I | H | —CH₃— | — | —SO₂— | —CH₂— | —CO₂C(CH₃)₃ | H |
| II | — | —CH₃ | — | —S— | —S— | —CO₂C(CH₃)₃ | H |
| II | — | —CH₃ | — | —CH₂— | —S— | —CO₂C(CH₃)₃ | H |
| III | — | — | H | —S— | —S— | —CO₂C(CH₃)₃ | H |

EXAMPLES

EXAMPLE 1

Preparation of acetic acid, [6-ethylidene-7-oxo-2,4-dithia-1-azabicyclo[3.2.0]hept-3-ylidene]-, 1,1-dimethylethyl[R-(E,E)]

Under a nitrogen atmosphere, 20 mg of

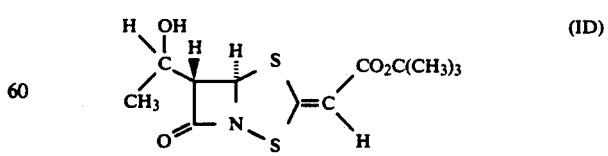

(ID)

were dissolved in 1.5 ml methylene chloride. This solution was cooled to −5° C. using a wet ice/acetone bath and 16 mgs of 4-dimethylamino pyridine were added, followed by addition of 0.0188 ml of benzyl chloroformate. The resulting mixture was stirred at −5° C. for 1 hr., at which time an additional 16 mg of 4-dimethylamino pyridine and 0.188 ml of benzyl chloroformate were added. This sequence was repeated two more times resulting in dissappearance of the starting material as monitored by thin-layer chromatography. The reaction mixture was quenched in 75 mls ethylacetate and 35 ml H₂O, the ethylacetate layer was separated, washed twice with H₂O, dried over Na₂SO₄, filtered and concentrated to yield a mixture of desired products. Separation and purification were achieved by column chromatography (silica gel/9:1 hexane:ethylacetate(EtOAc)) to yield 2-3 mgs of a 1:1 mixture of

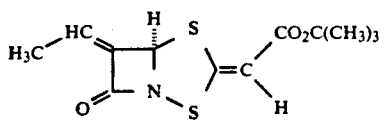
(II)

and 9 mgs of

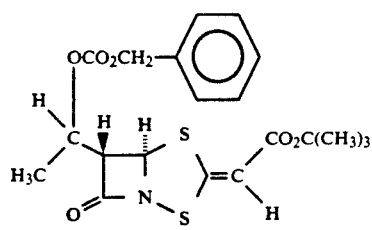
(I)

EXAMPLE 2

Preparation of acetic acid, [6-ethylidene-7-oxo-2-thia-1-azabicyclo[3.2.0]hept-3-ylidene],-1,1-dimethylethyl ester [R-(E,E)] and acetic acid, [7-oxo-6-[1-(((phenylmethoxy)carbonyl)oxy)ethyl]-2-thia-1-azabicyclo[3.2.0]hept-3-ylidene]-1,1-dimethylester [5R-[3R, 5.alpha., 6.alpha. (R))

Using the procedure described in *J. of Antibiotics* 36, p. 1034-39 (1983), a sufficient amount of compound IVA was prepared.

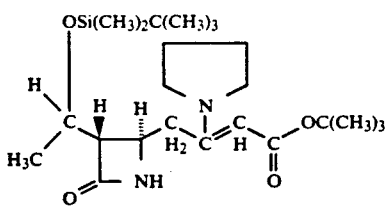
(IVA)

Under an N₂ atmosphere, 2.53 g of IVA were dissolved and combined with 12 mls Aldrich dry DHF. The mixture was cooled to 0° C. in an ice bath, and 0.45 mls of TFA was added over a 1 min. period, with stirring for about 1 min. The ice bath was removed and H₂S was bubbled in for 3 min. The mixture was stirred 5 min, quenched in 150 mls Et₂O/75 mls H₂O. The Et₂O layer was separated and, the aqueous layer was extracted with 75 ml fresh Et₂O. The Et₂O extracts were combined, washed three times with H₂O, concentrated, and chromatographed on silica gel using 2:1 hexane:EtOAc to yield 0.82 g of pale yellow oil (IVB), which was NMR consistent with the desired structure.

Under an N₂ atmosphere, 0.125 g of

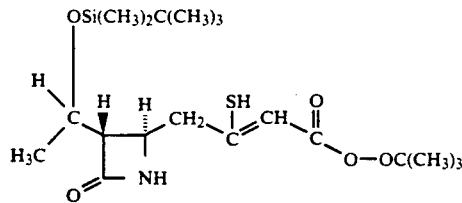

was dissolved in 20 ml CH₂Cl₂. The mixture was cooled to −20° C., 41 mg NCS were added, then 0.054 ml diisopropylethylamine in 5 cc CH₂Cl₂ was added dropwise. At the end of the addition, the mixture was checked by thin layer chromatography for disappearance of starting material, then washed three times with H₂O, once with brine, dried, concentrated, and chromotographed using (silica gel/9:1 hexane:EtOAc) to yield 5 mgs of lp isomer and 63 mg mp isomer. NMR data, H & C13 analysis were consistent with the desired structure. Based on NOE experiments, the major isomer was assigned the structure

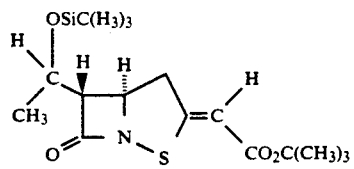

60 ml CCl₄ were degassed by bubbling N₂ through for 10-15 min, then the material was illuminated with a sun lamp for 9 hrs in a flask equipped with a reflux condensor. Product was isolated by column chromotography using 6:1 hexane:EtOAc.

Under a nitrogen atmosphere, 28.5 mgs of

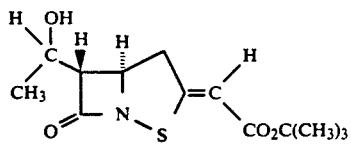
(IE)

were dissolved in 8 ml of dichloromethane. This solution was cooled down to −5° C. and 0.122 g of 4-dimethylamino pyridine was added, followed by addition of 0.144 ml benzylchloroformate. The rate of reaction, as monitored by thin layer chromatography (TLC), was very slow at −5° C. The reaction was allowed to warm to room temperature to increase the rate of reaction. An additional 0.122 g of 4-dimethylamino pyridine and 0.144 ml benzylchloroformate were added to the reation mixture. This sequence was repeated a total of four times at 1 hour intervals. Each time before addition, the reaction was cooled down to 5° C. then allowed to come to room temperature during the 1 hr. of stirring which preceeded the next addition. After the last addition TLC monitoring indicated only traces of starting material present. The reaction mixture was diluted with 75 ml ethylacetate, washed six times with H₂O, twice with 10 ml 1N HCL, four times with 25 ml H₂O, once with brine, dried over Na₂SO₄, filtered, concentrated, and the products purified and separated by column chromatography (silica gel/9:1 hexane:EtOAc) to yield 1 mg of a mixture of olefins

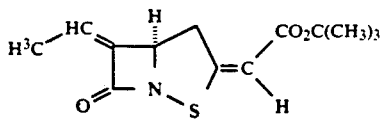

and 28.5 mgs of

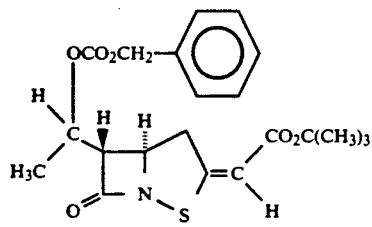

EXAMPLE 3

Preparation of acetic acid, [6-[1-[[(phenylmethoxy)carbonyl]oxy]ethyl]-7-oxo-2,4-dithia-1-azabicyclo[3.2.0]hept-3-ylidene]-,1,1-dimethyl ethyl ester, [5R-[3E, 5.alpha., 6.alpha. (R*)]]

Under an $N_2$ atmosphere, in a flask wrapped in aluminum foil to keep out light, 15 g of compound VB were dissolved with 50ml $CH_2Cl_2$, and stirred int. solution. To this was added 18 mls sodium ethyl hexanoic acid ethyl acetate (1 eq), then a mixture of 2 g of triphenylphosphine and 2 g of tetrakis(triphenylphosphine)palladium complex was added in one portion and allowed to stand as is. The mixture was TLC'd after 30 min, and showed some starting material remaining. To this was then added 0.4 g each of triphenylphosphine and tetrakis(triphenylphosphine)palladium complex. The mixture was allowed to stand 45 min more, then was quenched in 150 ml EtOAc and 50 ml 1N HCl, Ph 2.0. The organic layer was shaken and separated, washed once with $H_2O$, dried and concentrated to yield solids which were triturated with 125 mls $Et_2O$, filtered washed well with $Et_2O$ and dried to yield 9.2 g of solids having an NMR consistent the with desired structure.

Under an $N_2$ atmosphere, in equipment wrapped in aluminum foil for the purposes of keeping out light, 7.47 g of a starting trityl compound of the formula VC was dissolved in 75 mls of dichloromethane and 1.6 ml of methanol. To this mixture was added 4.3 ml pyridine. The resulting solution was cooled down to 0° C. and 5.85 g of

in 25 ml dichloromethane with enough methanol added to solubolize

was added dropwise. TLC performed 10 min. after completion of the addition indicated the dissappearance of starting material. The reaction was diluted to 125 mls with dichloromethane and washed once with 75 ml 1N HCL. The resulting suspension was filtered through a sintered glass funnel to yield 7.3 g of gray solids, after washing well with dichloromethane followed by hexane and air drying.

Under an $N_2$ atmosphere, these solids were suspended in 175 ml fresh $CH_2Cl_2$ amd cooled to 5° C. and with rapid stirring. $H_2S$ gas was bubbled through this suspension for 5 minutes, after which cooling was removed and the reaction mixture was stirred for 1 hr and 45 min. The reaction was then degassed by bubbling $N_2$ through, then filtered to remove the black gummy solids. The filtrates were dried over $Na_2SO_4$, filtered to remove $Na_2SO_4$, then cooled down to $-30°$ C. and 2.74 g of dicyclohexylcarbodimide in 25 mls of $CH_2Cl_2$ were added over a 5 min period. After the addition was complete, cooling was removed, the reaction was allowed to come to room temperature and was stirred for 1.5 hrs. Upon completion of stirring, the reaction was concentrated to ½ volume, the dicyclohexylurea was removed by filtration and the filtrates were chromatographed (silica gel/9:1 hexane:EtOAc) to yield 1.21 g of product of formula VD.

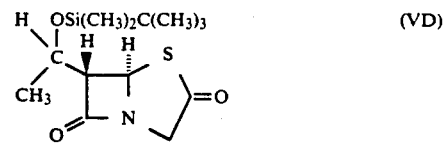

1.51 g of compound VD were combined with 1.88 g of (triphenyl)$P=CHCO_2C(CH_3)_3$ and 15 ml of benzene and heated at gentle reflux for 6 hours. The reaction was then concentrated and chromatographed (silica ge[/4:1 hexane:EtOAc) to yield 0.34 g of compound VE and 0.3 g of compound VF. Then under an $N_2$ atmosphere, 0.28 g of compound VD were dissolved in 5 ml of tetrahydrofuran and, 0.44 ml acetic acid and 2.1 ml of 1 molar tetrabutyl ammonium fluoride in tetrahydrofuran were added and the reaction mixture stirred at ambient temperature for 18 hrs. The reaction was worked up by diluting to 75 ml with ethyl acetate, washing three times with $H_2O$, once with brine, once with $H_2O$, once with brine, drying over $Na_2SO_4$, filtering, concentrating and chromatographing (silica gel/1:1 hexane:EtOAc) to yield 0.181 g of product.

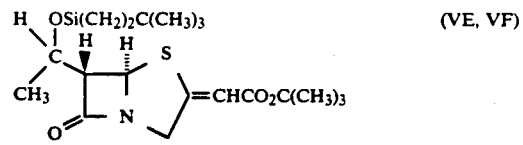

(Mixture of Stereoisomers)

Following the procedure of Example 2, 80 mgs of

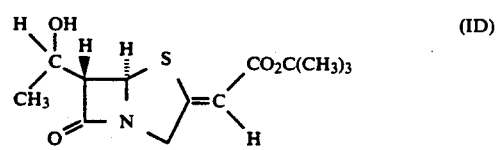

was converted to 0.11 g of the desired compound (I) wherein X and Y are both —S—, $R^1$ is phenylmethyloxycarbonyl, $R^2$ is methyl, B is t-butoxy and D is hydrogen:

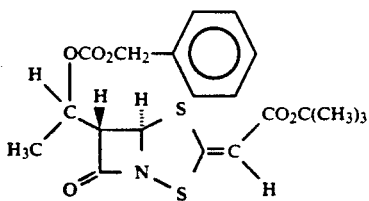
(I)

Oxidation Procedure

Under an $N_2$ atmosphere, 21 mg of the above form of compound I were dissolved in 1 ml of dichloromethane. The solution was cooled to 5° C. and 10 mg of 85% 3-chloroperoxybenzoic acid were added and the reaction allowed to stir 70 min. at which time thin layer chromatography indicated the presence of the two sulfoxides and just traces of starting material. The reaction was diluted with 25 mls ethyl acetate, and 10 ml $H_2O$, and enough Na bisulfite was added to give a negative test for peroxides using starch iodide test paper. The ethyl acetate layer was separated, washed three times with $H_2O$, once with brine, dried over $Na_2SO_4$, filtered, concentrated and chromatographed (silica gel/1:1 hexane:EtOAc) to yield 5.6 mgs. of the less polar isomer and 6.8 mgs. of the more polar isomer.

EXAMPLE 4

Preparation of propanoic acid, [2-[6 (1-hydroxyethyl)-7-oxo-2,4-dithia-1-azabicyclo [3.2 0] hept-3-ylidene]-,1,1-dimethylethyl ester, [5S-[3Z, 5.alpha., 6.alpha. (R*)]]

120 ml of 1M $LiN(Si(CH_3)_3)_2$ was added to a round bottom flask under nitrogen atmosphere and cooled down to −78° C. 16.2 ml (0.12 mol) of t-butyl acetate was added at such a rate as to maintain a temperature of −70° C. The mixture was allowed to stand at −70° C. for 10 min., after which 24 ml $CS_2$ were added. The mixture turned red and its temperature increased to −30° C. The mixture was then cooled back down to −70° C. and stirred for 10 min., then allowed to warm up to 0° C. and was finally cooled back down to −70° C. The mixture thickened. 16.25 ml (0.06 mol) of tributyltin chloride were added at such a rate so that the temperature remained at less than or equal to −60° C. The mixture then became clear and most of the red color disappeared. The mixture was then allowed to stand for 20 min. after which it was quenched with excess acetic acid in tetrahydrofuran at −60° C. The reaction mixture was added to 1.2 l hexane and 600 ml water were then added. The hexane layer was then separated and washed 5 times with 600 ml water, once with 600 ml brine, dried, and concentrated in vacuo to yield 29.5 g of a light orange oil of formula IA

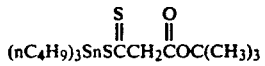
(IA)

The above product (ca 0.061 mol) was combined with 150 ml of dry tetrahydrofuran in a round bottom flask under nitrogen atmosphere and stirred into solution. The solution was cooled-down to −10° C. and 2.88 g of 50% sodium hydride (0.06 mol) was added. The mixture was then allowed to warm-up. After gas evolution ceased and a clear solution was obtained, 13.0 g (0.045 mol) of 3R, 4R-4-acetoxy-3-[1R-(dimethyl-t-butyl-siloxy) ethyl]2-azetidinone was added and allowed to stir for 12 hours. The reaction was worked up by quenching in 200 ml 1N HCl, and 500 ml ethyl acetate. The etryl acetate layer was then washed 4 times with 200 m water, once with 200 ml brine, dried, and concentrated to yield crude solid. The solid was then titrated with 175 ml hexane, filtered, washed 2 times with 15 al hexane and air dried to yield 8.89 g (47%) of product of formula IB as a pale yellow solid.

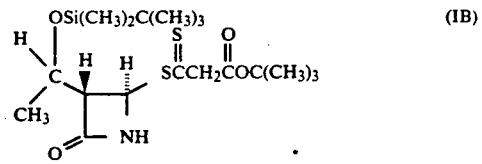
(IB)

(More product was obtained by chromatographing the mother liquor.)

9.35 g (0.022 mol) of the above product was dissolved in 225 ml methylene chloride in a round bottom flask under nitrogen atmosphere and stirred into solution. The solution was cooled to −20° C. and 2.96 g (0.022 mol) of N-chlorosuccinimide (NCS) was added. A methylene chloride solution (100 ml) containing 3.89 ml (0.022 mol) of diisopropyl ethylamine was then added to the solution over a 5 min. period. The solution was maintained at −20° C. under constant stirring. Thin layer chromatrography was performed 15 min. after addition of the base and indicated the reaction was complete. The solution was then diluted to 750 ml with methylene chloride, washed twice with 150 ml water, once with 100 ml brine, dried and concentrated and chromatographed on silica gel using 4:1 hexane:EtOAc to yield 8.8 grams (91%) of solids which was a 19:1 mixture of double bond isomers of [6-[1-[[(1,1-dimethylethyl)dimethylsilyl]oxy]ethyl]-7-oxo-2,4-dithia-1-azabicyclo[3.2.0]hept-3-ylidene]-, 1,1-dimethylethyl ester, [5R-[3E, 5.alpha., 6.alpha. (R*)]]-acetic acid, according to formula IC

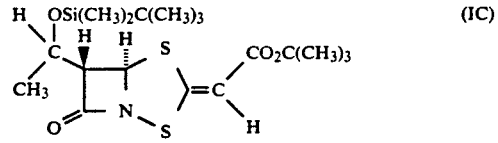
(IC)

8.8 g (0.021 mol) of the above product was combined with 155 ml tetrahydrofuran in a round bottom flask under nitrogen atmosphere and stirred into solution. 25.5 ml acetic acid was added, followed by 61.4 ml TBAF (tetrabutylammonium fluoride) in 1M THF and the reaction was stirred for 20 hrs. resulting in a pale yellow solution. The solution was worked-up in the usual manner, i.e., diluted with 750 ml ethylacetate, washed three times with 100 ml $H_2O$, once with 100 l brine, once with 100 l $H_2O$, once with 100 l brine, dried over $Na_2SO_4$, filtered, concentrated and triturated with isopropyl ether to give product (4.64 g). An additional 0.53 g was obtained upon chromatography of the mother liquor (50:50 hexane: ethyl acetate), totalling 5.17 g (81%) of propanoic acid, [2-[6-(1-hydroxyethyl)-7-oxo-2,4-dithia-1-azabicyclo [3.2.0]hept-3-ylidene]-, 1,1-diemthyl ethyl ester, [5S-[3Z, 5.alpha., 6.alpha. (R*)]] product of formula ID

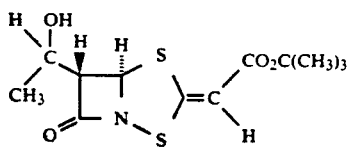 (ID)

EXAMPLE 5

Preparation of acetic acid, [7-oxo-6-[1-[[-(1,1-dimethyloxy)carbonyl]oxy]ethyl]-2-thia-1-azabicyclo[3.2.0]hept-3-ylidene]-, 1,1-dimethyl ethyl ester, [5R-[3E, 5.alpha., 6.alpha. (R*)]]

15 mg of propanoic acid, [2-[6-(1-hydroxyethyl)-7-oxo-2,4-dithia-1-azabicyclo[3.2.0]hept-3-ylidene]-,1,1-dimethyl ethyl ester, [5X-[3Z,5.alpha.)6.alpha.(R*)]], prepared according to Example 4 was dissolved in 1.5 ml CDCl3 in a flask under nitrogen atmosphere and cooled to −5° C. in a mixed ice/acetone bath. 6 mg Dimethylaminopyridine (DMAP) was added followed by 0.06 ml pivaloylchloride and stirred for 30 min. To this was added 12 mg DMAP and 0.12 ml pivaloylchloride, with stirring for a further 30 min. TLC indicated the continued presence of starting material. A further 12 mg DMAP and 0.12 ml pivaloylchloride were added with stirring for a further 30 min. TLC was repeated and indicated the continued presence of a small amount of starting material. A portion of the sample was checked by NMR and showed a ratio of product to starting material of approximately 4:1. The addition of 12 mg DMAP and 0.012 ml pivaloylchloride was repeated one more time. TLC indicated the remaining presence of traces of starting material. The mixture was then diluted to 50 cc with ethyl acetate, washed 3 times with 10 cc water and dried and concentrated in vacuo. Silica gel chromatography using 3:1 hexane: ethyl acetate afforded 16.2 mg product (84%) acetic acid, [7-oxo-6-[1-[[(1,1-dimethyloxy)carbonyl]oxy]ethyl]-2-thia-1-azabicyclo[3.2.0]hept-3-ylidene]-, 1,1-dimethyl ethyl ester, [5R-[3E, 5.alpha., 6.alpha. (R*)]].

Protocol

In order to screen compounds prepared according to the present invention for their relative efficacy as elastase inhibitors, the protocol Enzyme Assays for the Inhibition of Human Polymorphonuclear Leukocyte Elastase Via Hydrolysis of N-t-Boc-alanyl-alanyl-prolylalanine-p-nitroanilide was followed.

This protocol utilizes these reagents:
0.05 M TES (N-tris[hydroxymethyl]methyl-2-aminoethanesulfonic acid) Buffer, pH 7.5;
0.2 mM N-t-Boc alanyl-alanyl-prolyl-alanine-p-nitroanilide (Boc-AAPAN).

The substrate was first prepared by dissolving the solid (m.w. 550) in 10.0 ml dimethylsulfoxide (DMSO). Buffer was then added to attain a final volume of 100 ml.

The protocol also utilizes:
A crude extract of human polymorphonuclear leckocytes (PMN) containing elastase activity; and
inhibitors (cephalosporin esters) to be tested, which were dissolved in DMSO just before use.

The assay procedure followed as part of the protocol was to add from 0.01 to 0.1 ml of DMSO, with or without inhibitor, to 1.0 ml of 0.2 mM Boc-AAPAN, in a cuvette. After mixing, a measurement was taken at 410 mμ to detect any spontaneous hydrolysis due to presence of the test compound. To this was then added 0.05 ml of PMN extract and the rate of change of optical density (ΔOD/min) was measured and recorded at 410 mμ using a Beckman Model 35 spectrophotometer.

We claim:
1. A compound of the formula I, II or II

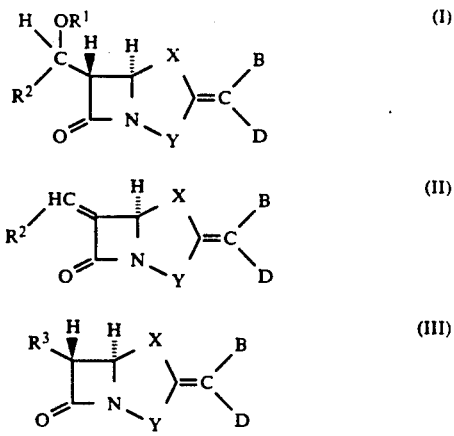

wherein
X and Y are each —S— or —CH2—, with at least one of X and Y being —X—, or alternatively, X is 13 SO— or —SO2— and Y is —CH2—;
$R^1$ is selected from the group consisting of hydrogen, tri(lower alkyl)silyl, —COOR" and —CONHR''', wherein
R" and R''' are each selected form the group consisting of lower alkyl and phenyl(lower alkyl);
$R^2$ is lower alkyl;
$R^3$ is selected from the group consisting of hydrogen, lower alkyl and lower alkoxy;
one of B and D is selected from the group consisting of (lower alkyl)oxycarbonyl, (lower alkenyl)oxycarbonyl, allyloxycarbonyl and phenyl (lower alkyl)oxycarbonyl: and
the other of B and D is selected from the group consisting of hydrogen and lower alkyl:
wherein the term lower includes both straight and branched chains having from 1 to 6 carbon atoms.

2. A compound according to claim 1 wherein D is hydrogen.

3. A compound of formula I according to claim 1 wherein $R^1$ is selected from the group consisting of hydrogen, benzylaminocarbonyl and benzoxycarbonyl; and D is selected from the group consisting of lower alkyl and hydrogen.

4. The compound according to claim 3 wherein $R^1$ is hydrogen, $R^2$ is methyl, B is t-butoxycarbonyl and D is hydrogen.

5. The compound according to claim 3 wherein $R^1$ is hydrogen, $R^2$ is methyl, B is benzoxycarbonyl and D is hydrogen.

6. The compound according to claim 3 wherein $R^1$ is hydrogen, $R^2$ is methyl, B is allyloxycarbonyl and D is hydrogen.

7. The compound according to claim 3 wherein $R^1$ is hydrogen, $R^2$ is methyl, B is t-butoxycarbonyl and D is methyl.

8. A compound according to claim 3 wherein X and Y are both —S—.

9. A compound of formula II according to claim 1 wherein R² is methyl and D is selected from the group consisting of hydrogen and lower alkyl.

10. A compound according to claim 9 wherein D is hydrogen.

11. A compound according to claim 10 wherein B is t-butoxycarbonyl.

12. A compound according to claim 9 wherein X and Y are both —S—.

13. A compound according to claim 9 wherein X is —CH₂—, Y is —S—, B is t-butoxycarbonyl and D is hydrogen.

14. A compound of formula III according to claim 1 wherein R³ is hydrogen and D is selected from the group consisting of lower alkyl and hydrogen.

15. A compound according to claim 14 wherein D is hydrogen.

16. A compound according to claim 15 wherein B is t-butoxycarbonyl.

17. A compound according to claim 14 wherein X is —S— and Y is —CH₂—.

18. A compound according to claim 14 wherein X and Y are both —S—.

19. A compound according to claim 3 wherein X is —CH₂ and Y is —S—.

20. A compound according to claim 3 wherein X is —S— and Y is —CH₂—.

21. A compound according to claim 3 wherein X is —SO— or —SO₂—.

22. A compound according to claim 9 wherein X is —SO— or —SO₂—.

23. A pharmaceutical preparation for the treatment of inflammatory conditions in human beings, including adult respiratory distress syndrome, pulmonary emphysema bronchial inflammation, osteo arthritis, spondylitis, lupus, psoriasis and rheumatoid arthritis comprising an effective amount of a compound of the general formula I, III or III:

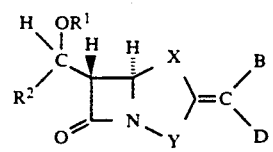 (I)

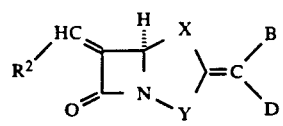 (II)

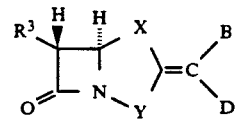 (III)

wherein:
X and Y are each —S— or —CH₂—, with at least one of X and Y being —S—, or alternatively, X is —SO— or —SO₂— and Y is —CH₂—;
R¹ is selected from the group consisting of hydrogen, tri (lower alkyl) silyl, —COOR" and —CONHR'", wherein
R" and R'" are each selected form the group consisting of lower alkyl and phenyl (lower alkyl);
R² is lower alkyl;
R³ is selected from the group consisting of hydrogen, lower alkyl and lower alkoxy;
one of B and D is selected from the group consisting of (lower alkyl) oxycarbonyl, allyloxycarbonyl and phenyl (lower alkyl) oxycarbonyl; and
the other of B and D is selected form the group consisting of hydrogen and lower alkyl;
wherein the term lower includes both straight and branched chains having from 1 to 6 carbon atoms; together with a pharmaceutically acceptable diluent or carrier.

* * * * *